(12) United States Patent
Tominaga et al.

(10) Patent No.: US 7,399,371 B2
(45) Date of Patent: Jul. 15, 2008

(54) TREATMENT METHOD FOR IMPROVING FATIGUE LIFE AND LONG-LIFE METAL MATERIAL TREATED BY USING SAME TREATMENT

(75) Inventors: Tomonori Tominaga, Futtsu (JP); Kazumi Matsuoka, Futtsu (JP); Tadashi Ishikawa, Futtsu (JP); Tadashi Kasuya, Futtsu (JP); Koji Homma, Futtsu (JP)

(73) Assignee: Nippon Steel Corporation, Tokyo (JP)

( * ) Notice: Subject to any disclaimer, the term of this patent is extended or adjusted under 35 U.S.C. 154(b) by 434 days.

(21) Appl. No.: 10/826,772

(22) Filed: Apr. 16, 2004

(65) Prior Publication Data

US 2005/0230010 A1    Oct. 20, 2005

(51) Int. Cl.
*C21D 1/55* (2006.01)
(52) U.S. Cl. .................. 148/508; 266/99; 72/53
(58) Field of Classification Search .............. 266/44, 266/99; 148/508, 558; 72/53
See application file for complete search history.

(56) References Cited

U.S. PATENT DOCUMENTS

| | | | |
|---|---|---|---|
| 5,625,664 A | 4/1997 | Berkley | |
| 6,289,705 B1 * | 9/2001 | Duquenne et al. | 72/53 |
| 6,338,765 B1 | 1/2002 | Statnikov | |
| 6,467,321 B2 * | 10/2002 | Prokopenko et al. | 72/53 |
| 6,926,780 B2 * | 8/2005 | Xiong et al. | 148/558 |
| 2002/0056303 A1 * | 5/2002 | Berthelet et al. | 72/53 |
| 2002/0069687 A1 * | 6/2002 | Berthelet et al. | 72/53 |
| 2002/0124402 A1 * | 9/2002 | Berthelet et al. | 29/889.1 |
| 2002/0189726 A1 * | 12/2002 | Statnikov | 148/558 |

FOREIGN PATENT DOCUMENTS

| | | |
|---|---|---|
| CA | 2 491 743 | 2/2004 |
| JP | 2003-113418 | 4/2003 |
| WO | WO 00/39567 | 7/2000 |

OTHER PUBLICATIONS

"Surface Nanocrystallization (SNC) of Metallic Materials-Presentation of the Concept behind a New Approach" J. Mater. Sci. Technol., vol. 15 No. 3, 1999, pp. 193-197, Dec. 1999.

* cited by examiner

*Primary Examiner*—Scott Kastler
(74) *Attorney, Agent, or Firm*—Kenyon & Kenyon LLP

(57) ABSTRACT

A novel treatment method, for improving fatigue life, is provided that aims to resolve problems associated with conventional treatment methods for improving fatigue life of metal by reduction of stress concentration and conventional treatment methods for improving fatigue life of metal by introduction of compressive stress, that is, problems of poor efficiency in work execution, required level of skill of workers, and the impossibility of quality control due to lack of means for measuring the effect after treatment, characterized in that, for locations in metal for which fatigue is a problem, after pre-treatment is performed, ultrasonic impact treatment is performed, and thereafter, a quality assurance test is performed so as to improve the fatigue life of the metal.

2 Claims, 2 Drawing Sheets

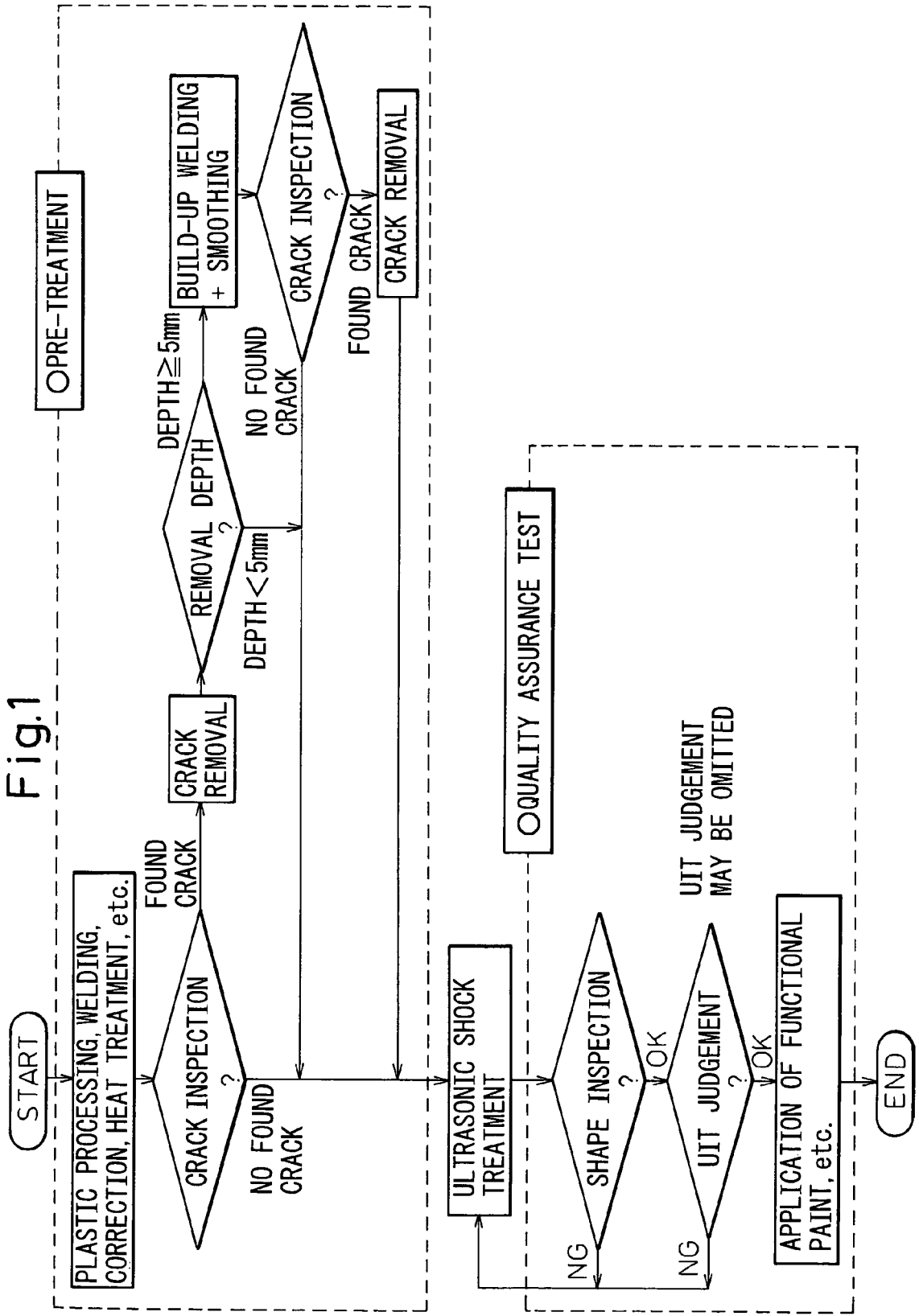

TREATMENT METHOD FOR IMPROVING FATIGUE LIFE AND LONG-LIFE METAL MATERIAL TREATED BY USING SAME TREATMENT

TECHNICAL FIELD OF THE INVENTION

The present invention relates to metal products such as large welded structures, e.g. a bridge, etc., welded metal products, e.g. a base carrier of an automobile, etc., non-welded metal products such as a vehicle wheel, etc. and, more particularly, to a treatment method for improving fatigue life that increases durability, with respect to fatigue crack, and especially in locations likely to be impaired by fatigue, in order to permit the useful life to be lengthened, and to a metal material treated by using same treatment method.

DESCRIPTION OF THE BACKGROUND ART

The durability of a metal product is often determined by the fatigue strength of the product. In order to increase the fatigue strength, a general practice is to increase the design cross-section to thereby reduce stress. However, various other treatment methods may be employed to improve fatigue characteristics.

Treatment methods for improving fatigue characteristics may be broadly divided into two types. One type includes those methods, such as grinding and TIG dressing, which aim to reduce stress concentration by modifying the shape of the parts likely to be affected by fatigue. The other type includes those methods, such as hammer peening, needle peening, shot peening, welding using low temperature transformation material, etc., which aim to reduce the effective range of repeated stress by imparting compressive residual stress to the parts likely to be affected by fatigue. The above-mentioned hammer peening is considered to have both effects, that is, reduction of stress concentration and introduction of compressive residual stress.

Among the above-described treatment methods for improving fatigue characteristics, the methods that aim to reduce stress concentration have an effect that is evidently visible to the eye. In practice, however, when there is a minute flaw in the spot likely to be affected by fatigue, it may degrade the fatigue strength. Therefore, in order to be effective, the grinding treatment requires high skill and the execution of the treatment work may require much time. These factors result in a considerable increase in the cost.

Also, with respect to TIG dressing, highly skilled workers are required for the execution of the treatment work. As heat is applied to the treated site, in the case where this method is applied to repair a bridge beam, traffic must be stopped while the treatment work is being executed in order to avoid the occurrence of hot cracking of welding material due to stress variation. This is also a considerable cost factor.

On the other hand, in those methods which aim to introduce compressive residual stress, the compressive residual stress is not visible to the naked eye, and the effect of the treatment is difficult to measure and cannot be readily assured by inspection. Thus, in view of quality control, this type of treatment is usually not adopted unless an engineer competent in diagnosis and judgement can attend to the treatment work at the site.

In case of hammer peening, large plastic deformation can be imparted to the treated part, and since a large treatment mark is left, treatment can be identified after the work. A surface flaw that is produced at the time of treatment, however, may bring about stress concentration and result in degradation of fatigue strength. In addition, as workability is poor due to the large reaction produced when the plastic deformation is imparted, fine control is difficult and quality control becomes very difficult.

Especially when the treatment method for improving fatigue characteristics by introducing compressive residual stress as described above is applied, if there are cracks of 1 mm or less in length, which represent an early stage of occurrence of fatigue cracks and which cannot be detected by current examination methods such as liquid penetrant examination, magnetic particle examination, eddy current examination, or the like, application of the above-described treatment method for improving fatigue life in the presence of such cracks cannot stop the propagation of the cracks. Thus, it is considered that the introduction of compressive residual stress has little or no effect in improving fatigue life.

Also in the case of introducing compressive residual stress to a toe portion by welding using low temperature transformation material, although this treatment has large effect in high strength steel, it has little or no effect in low strength steel. In addition, as heat is applied in welding, it has the same problem in execution of work as in TIG dressing and is difficult to use in practice. Also, as in other treatment methods, effect of the introduced compressive residual stress is difficult to measure.

As has been described above, in the case of treatment methods for improving fatigue characteristics that aim to reduce stress concentration, there are problems mainly in efficiency of work execution and the skill required of workers. On the other hand, in the case of treatment methods for improving fatigue characteristics that introduce compressive residual stress, there are problems that effect of the treatment cannot be measured and quality control is not possible. Therefore, these treatment methods for improving fatigue characteristics are generally difficult to use.

SUMMARY OF THE INVENTION

It is an object of the present invention to resolve the above-described problem and to provide a treatment method for improving fatigue characteristics which permits long useful life to be achieved and to a long life metal product treated by using the same treatment method, wherein, as the treatment method for improving fatigue characteristics, metal surface is subjected to peening by ultrasonic impact using a tool with a tip ultrasonically vibrated in an amplitude of 20 μm~60 μm at frequency of 15 kHz~60 kHz in a treatment called an ultrasonic impact treatment, in conjunction with pre-treatment and inspection which takes into consideration characteristics imparted to the metal by the ultrasonic impact treatment so as to assure effect of the treatment.

In order to attain above object, in accordance with a first aspect of the present invention, a treatment method is provided and characterized in that, after a pre-treatment is performed, an ultrasonic impact treatment is performed on the spot likely to be affected by fatigue of metal material, and thereafter, quality assurance examination is performed, to improve the fatigue life of the metal material.

In accordance with a second aspect of the invention, a treatment method is provided, wherein, after a processing is performed in the pre-treatment according to the first aspect above, such as plastic processing, deformation correction, heat treatment, welding, etc., which modifies internal stress and/or surface stress of the metal material at or near the spot to be subjected to the ultrasonic impact treatment, the ultrasonic impact treatment is performed, and no further processing which modifies internal stress and/or surface stress of the metal material is performed after the ultrasonic impact treatment.

In accordance with a third aspect of the invention, a treatment method is provided, wherein, after a processing is performed in the pre-treatment according to the first aspect above, such as plastic processing, deformation correction, heat treatment, welding, etc., which modifies internal stress and/or surface stress of the metal material at or near the location to be subjected to the ultrasonic impact treatment, a non-destructive examination and the ultrasonic impact treatment are performed, and no further processing, which modifies internal stress and/or surface stress of the metal material, is performed after the ultrasonic impact treatment.

In accordance with a fourth aspect of the invention, a treatment method is provided, wherein, in the pre-treatment according to the first aspect above, a visual inspection, a liquid penetrant examination, a magnetic particle examination, an eddy current examination or the like, is performed, and upon detection of a crack, the crack is removed by grinding, gouging or the like.

In accordance with a fifth aspect of the invention, a treatment method is provided, wherein, in the crack removal according to the fourth aspect above, if the depth of the removal is as deep as 5 mm, after build-up welding is performed and is finished smooth with a grinder, a visual inspection, a liquid penetrant examination, a magnetic particle examination, an eddy current examination or the like, is further performed, to ensure that no crack can be detected.

In accordance with a sixth aspect of the invention, a treatment method is provided, wherein, in the ultrasonic impact treatment according to the first aspect above, the treatment is performed on a toe portion, a HAZ portion, and a welded portion of welded metal material to modify the shape such that stress concentration is unlikely, and at the same time, compressive residual stress is introduced so as to render minute defects harmless as the origins of fatigue cracks and to suppress the occurrence of cracks.

In accordance with a seventh aspect of the invention, a treatment method is provided, wherein, in the ultrasonic impact treatment according to the first aspect above, the treatment is performed on the cut section or its vicinity of metal material that is cut with a saw, shear, gas, laser, plasma, or the like, so as to modify the shape such that stress concentration is unlikely, and at the same time, compressive residual stress is introduced so as to render minute defects or extremely hardened portions harmless as the origins of fatigue cracks and to suppress occurrence of cracks.

In accordance with an eighth aspect of the invention, a treatment method is provided, wherein, in the ultrasonic impact treatment according to the first aspect above, compressive stress is introduced to cracks not greater than the detection limit of non-destructive examination using impact by the ultrasonic impact treatment in order to stop the propagation of the cracks.

In accordance with a ninth aspect of the invention, a treatment method is provided, wherein, in the ultrasonic impact treatment according to the first aspect above, two passes or more of the ultrasonic treatment are performed on the same spot of a structure where occurrence of a fatigue crack is likely in order to introduce compressive stress to cracks not greater than the detection limit of non-destructive examination using impact by the ultrasonic impact treatment in order to reliably stop the propagation of the cracks.

In accordance with a tenth aspect of the invention, a treatment method is provided, wherein, in the quality assurance examination according to the first aspect above, the shape of the surface after the ultrasonic impact treatment is reproduced by using molding material such as dental shaping agent or by scanning with a high precision instrument such as a laser displacement meter, in order to ensure that the treated surface has approximately the same radius of curvature as the R (radius) of the tool tip used in the ultrasonic impact treatment, and that plastic deformation has been produced at depth of 0.05 mm or more by the treatment, thereby to confirm that the shape is improved at the treated spot and compressive residual stress has been introduced to improve fatigue life.

In accordance with an eleventh aspect of the invention, a treatment method is provided, wherein, in the quality assurance examination according to the first aspect above, when the ultrasonic impact treatment is performed as a stationary process, the tool tip used in the ultrasonic impact treatment is identified, the output setting of the apparatus is checked and the occurrence of plastic deformation at the treated spot is confirmed by visual inspection, thereby to confirm that the shape is improved at the treated spot and compressive residual stress has been introduced to improve fatigue life.

In accordance with a twelfth aspect of the invention, a treatment method is provided, wherein, in the quality assurance examination according to the first aspect above, if it is doubtful whether the deformation is produced by the ultrasonic impact treatment, in the measurement of the deformation formed on the metal surface, a SUMP method is used to replicate the treated surface and to observe the metallographic microstructure of the topmost surface, thereby to confirm that the surface microstructure of the treated portion is finer than that of untreated portion and to determine that the deformation is formed by the ultrasonic impact treatment.

In accordance with a thirteenth aspect of the invention, a treatment method is provided, wherein, in the quality assurance examination according to the first aspect above, if it is doubtful whether the deformation is produced by the ultrasonic impact treatment, in the measurement of the deformation formed on the metal surface, particle size at the topmost metal surface of the treated spot is measured with an ultrasonic grain size measurement instrument, thereby to confirm that the surface microstructure of the treated portion is finer than that of untreated portion and to determine that the deformation is formed by the ultrasonic impact treatment.

In accordance with a fourteenth aspect of the invention, a treatment method is provided, wherein, in the quality assurance examination according to the first aspect above, if it is doubtful whether the deformation is produced by the ultrasonic impact treatment, in the measurement of the deformation formed on the metal surface, surface roughness of the treated surface is measured with a roughness meter or a laser displacement meter, thereby to confirm that, in the direction perpendicular to the formed curve with a radius R, the surface is smoother than that of untreated portion, and to determine that the deformation is formed by the ultrasonic impact treatment.

In accordance with a fifteenth aspect of the invention, a treatment method is provided, wherein, in the quality assurance examination according to the first aspect above, if it is doubtful whether the deformation is produced by the ultrasonic impact treatment, in the measurement of the deformation formed on the metal surface, hardness of the treated surface is measured using Vickers test or the like, thereby to confirm that the surface hardness is increased by not less than 20% and less than 100% compared to the other untreated portion and to determine that the deformation is formed by the ultrasonic impact treatment.

In accordance with a sixteenth aspect of the invention, a treatment method is provided, wherein, in the quality assurance examination according to the first aspect above, paint is coated such that, when a crack occurs during subsequent usage in the ultrasonic impact treated portion after passing the quality assurance examination, a micro-capsule contained within the painted film is broken at the crack and a paint of different color seeps out to indicate the occurrence of a crack so that occurrence of a crack can be easily recognized.

In accordance with a seventeenth aspect of the invention, a metal material is provided, characterized in that the metal material is treated using the processing method for improving fatigue life according to any one of the first to sixteenth aspects of the invention.

BRIEF DESCRIPTION OF THE DRAWINGS

FIG. 1 is a flow chart showing a treatment method for improving fatigue life according to the present invention;

DESCRIPTION OF THE MOST PREFERRED EMBODIMENT

Figure 2A:
FIG. 2(a) is a view showing the smoothness of a metal surface after finishing with a grinder.

Occurrence of fatigue fracture in metal is greatly influenced by stress concentration and residual stress. When a metal material is subjected to load, dislocations tend to accumulate at the point of stress concentration, and as a result, slip lines accumulate there and develop into a crack, and the crack develops and propagates after it is produced. Residual stress is usually present as tensile residual stress at welded portion or the like, and is considered to enlarge the range of repeated stress and help to give rise to a crack as well as to promote opening of the produced crack. Therefore, in order to improve fatigue life of a metal material, it is necessary to relieve the stress concentration and to realize compressive residual stress as far as possible.

A welded point of a metal material contains both sharp change in surface shape and tensile residual stress, and therefore, constitutes the weakest point with respect to fatigue strength. The sharp change in surface shape acts as a notch to induce stress concentration. Therefore, in order to relieve stress concentration, it is important to impart plastic deformation to the point of stress concentration and thereby to form a smooth curved surface with toe of large radius of curvature. If, at this time, plastic deformation is imparted to the metal in the direction of plate thickness, compressive stress can be introduced by constricting the plasticized metal with a surrounding metal.

A cut end section of a metal material contains a sharp change of surface shape and tensile stress and shear stress associated with the cutting and, therefore, also constitutes a weak point with respect to fatigue. In this case, too, by imparting plastic deformation in the direction perpendicular to the end section, or by imparting plastic deformation so as to form curved surface at the edge of the end section, improvement of surface shape and introduction of compressive stress is possible.

As means that permit such plastic processing to be performed, a treatment called ultrasonic impact treatment is known, wherein peening is performed to impart impact to metal surface using a tool with tip ultrasonically vibrated in an amplitude of 20 μm~60 μm at frequency of 15 kHz~60 kHz. By using this method, plastic processing can be performed on metal surface and compressive residual stress can be introduced to a depth of about 1.5 mm.

This method of ultrasonic impact treatment is basically the same as hammer peening in basic mechanism for improving fatigue strength. Thus, although the energy of each individual impact is small, ten thousand or more impacts are imparted to the metal surface and similar plastic deformation can be realized as in hammer peening. As the force of each individual impact is small, there is little or no reaction to the apparatus, and therefore, this method is very advantageous in tool usage and workability compared to hammer peening.

As impact is imparted to the metal surface many times in the ultrasonic impact treatment, an effect that cannot be obtained in conventional hammer peening is produced in the steel surface. As the energy of each individual impact is larger than in shot peening, an effect which cannot be obtained in conventional shot peening is produced.

As impact is imparted to the metal surface many times, almost complete homogeneity of treatment can be achieved. It is known that, even in the case of hammer peening, homogeneity of treatment can be achieved to some degree when several passes are performed on the same line. But, in the case of ultrasonic impact treatment, the rate of impact is 15,000 to 60,000 times per second, and homogeneity of treatment that can be achieved is at quite a different level than in hammer peening. With speed of treatment of about 0.5 m/min, homogeneity of the finished metal surface is almost complete, leaving no defect at all.

Figure 2B:
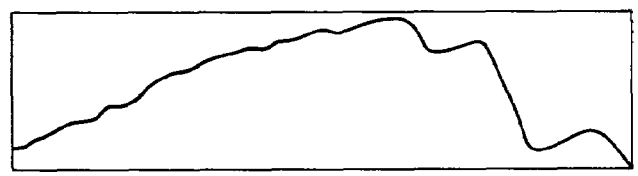
FIG. 2(b) is a view showing the smoothness of a metal surface after the ultrasonic impact treatment according to the present invention.

The metal surface after the treatment has remarkable smoothness. From the comparison of the smoothness of the metal surface before and after the treatment as shown in FIG. 2(a) and FIG. 2(b), it can be seen that the metal surface after the ultrasonic impact treatment is significantly smoother than the metal surface after finishing with a grinder.

It has been found that the metallographic microstructure of the metal surface after treatment is rendered remarkably fine by repeated plastic processing using ultrasonic wave (Surface Nanocrystallization (SNC) of Metallic Material—Presentation of the Concept behind a New Approach, J. Master. Sci. Technol., Vol. 15, No. 3, 1999).

In fact, as a result of ultrasonic impact treatment used for improving fatigue characteristics, it has been found that the microstructure of a steel material is greatly changed after the treatment. The effect of the treatment, as seen in the achieved fine microstructure of steel material, is especially remarkable in a HAZ portion near the welding where steel microstructure tends to be coarseened. After the ultrasonic impact treatment, the grain size in HAZ portion, that is usually as coarse as 100 μm, is reduced to almost below detection limit, and a unique steel microstructure which does not permit grain size to be observed is achieved by the ultrasonic impact treatment.

Figure 3:
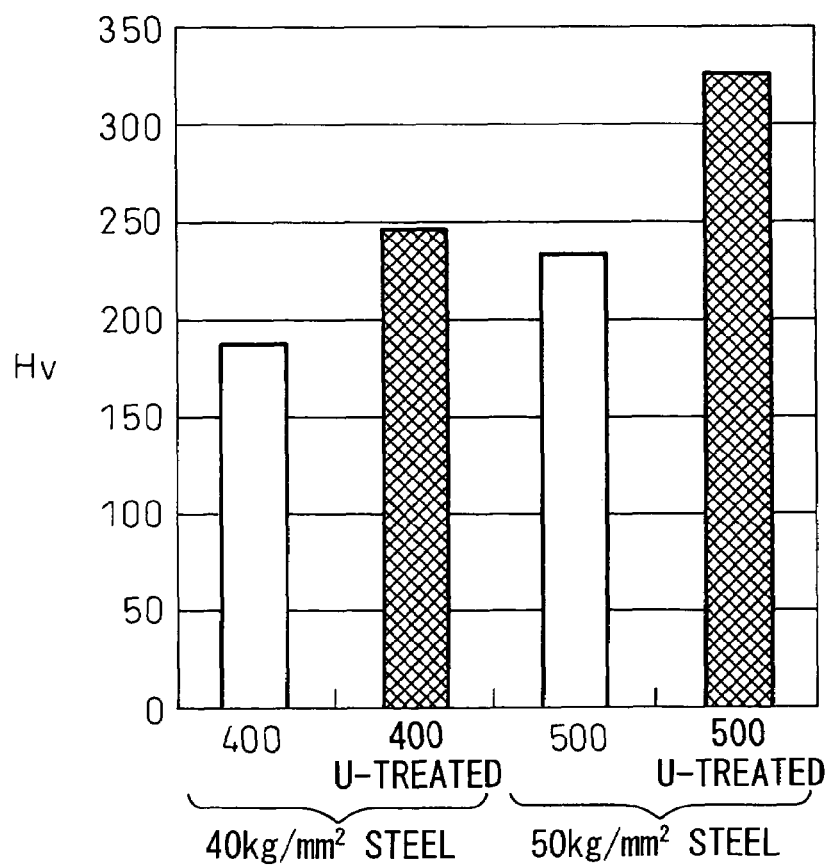
FIG. 3 is a view showing the comparison of the hardness of a metal surface before and after the ultrasonic impact treatment according to the present invention.

As the microstructure at the steel surface becomes finer by ultrasonic impact treatment, the hardness increases. Distribution of hardness in the mother material, weld metal portion and HAZ portion is shown in FIG. 3. It can be seen that, in the case of steel having strength commonly used in welded steel structures, hardness increases by 20% or more in the steel treated by using ultrasonic impact treatment as indicated by U-treated. Depending upon the material and the duration of treatment, hardness increases up to about twice the value before the treatment. This does not mean, however, that the steel is transformed into a martensite that is hard and fragile. An increase in hardness is mainly due to finer grain size and work hardening caused by accumulation of dislocations, and therefore, is not such an increase in hardness as would give rise to a weld cracking.

Fatigue fracture of a steel plate is composed of generation of a crack and propagation of the crack. A sum of a crack generation life and a crack propagation life is the total life time leading to the fatigue crack. A crack generates often at the point of high stress concentration or high residual stress. The generated crack continues to propagate, and finally leads to fracture of the member. In order to increase the life time determined by fatigue fracture, it is necessary to suppress generation of a fatigue crack and propagation of the fatigue crack.

Usually, however, once a crack is generated in a steel material, the stress concentration at the tip of the crack is quite large, and it is extremely difficult to stop the propagation of the crack. For example, even if a stop hole is drilled at the tip and the hole is tightly bound with a high strength bolt, when the tip of the crack is left, the crack may propagate into the bolt and may lead to breakage.

A fatigue crack in the initial stage can be observed by detecting the generation of crack from measurement of the strain in a fatigue test of a boxing specimen. When the fatigue crack in the initial stage at the time of detecting the generation of crack is observed, it is found that about one tenth of the ordinary fatigue life time of the boxing joint has elapsed at this time point. The remaining nine tenths of the life time is the propagation life of the crack. Thus, the remaining life time of the joint is practically determined unless the crack is removed.

However, the crack at this stage cannot be detected by ordinary method such as liquid penetrant test, or magnetic particle test. If a conventional treatment for improving fatigue life such as hammer peening, shot peening, is performed in this state, the treatment may leave the crack intact. Thus, although plastic deformation appears to be produced in the treated surface, propagation of the crack cannot be stopped and an improvement effect may be limited to that due to reduction of stress concentration by improved shape, resulting in little or no increase of fatigue life.

However, if ultrasonic impact treatment is performed in this state, compressive stress is introduced by plastic deformation to a depth of about 1.5 mm, and the crack can be broken down so as to prevent the tip of the crack from being opened. Although compressive stress can be introduced to a comparable depth by hammer peening, the effect of treatment by hammer peening is uneven and may leave the crack intact. In this respect, a remarkably large number of impacts are imparted to the surface in ultrasonic impact treatment, and opening of the crack can be suppressed uniformly and reliably.

Therefore, in order to achieve an improvement in the fatigue life effectively, a basic procedure is to perform ultrasonic impact treatment on welded metal products centered on toe portion of welding, and on weld metal portion and HAZ portion. The boundary between the weld metal and HAZ is the weakest point with respect to fatigue. This boundary can be reinforced with respect to fatigue, and an adverse effect of the high temperature cracking produced on the surface of the weld metal can be significantly relieved. It should be noted that the treatment is considered to have little effect on hydrogen cracking at low temperature.

A cut section of metal cut by a saw, shear, gas, laser, plasma, etc., is also a weak point with respect to fatigue even if no welding is performed. Ultrasonic impact treatment is performed on the cut end surface to increase fatigue life effectively. By this treatment, excessive tensile stress and shear stress introduced by cutting is relieved. Further, compressive stress is introduced, and stress concentration points such as a burr produced in cutting work is shaped into smooth curved surface by plastic deformation. In addition, an extremely hardened layer, produced at the end surface by the cutting method accompanied by application of heat such as gas, laser, plasma, etc., can be made harmless. Care should be exercised at this time lest an excessively large output imparts harmful deformation to the end surface. This is not possible with conventional hammer peening, is inefficient with shot peening, and is only possible with ultrasonic impact treatment that has little reaction and can be controlled easily.

For treatment of the welded portion or the cut end section, one pass of treatment is sufficient as the number of treatment per one treatment line. However, when higher uniformity is desired, or when input power per treatment is to be kept low in order to achieve better control or to avoid excessive plastic deformation, two passes or more of treatment may be performed on the same line to obtain more reliable effect in fatigue life improvement.

As has been described above, the microstructure of a metal subjected to ultrasonic impact treatment undergoes a unique change as compared to the effect of other treatment methods for improving fatigue life that employ introduction of compressive stress. Therefore, it is relatively easy to determine, from observation of surface roughness, hardness, and microstructure (grain size) of the treated metal surface, whether or not the mark of plastic deformation on a metal surface is produced by ultrasonic impact treatment.

The surface state after treatment can be observed by preparing a copy of the surface using a SUMP method or can be directly measured by scanning with a displacement meter. Hardness can be easily measured using Vickers test or the like. When only the grain size is to be measured, an ultrasonic grain size analyzer can be conveniently used.

The extent of stress concentration can be easily determined by measuring the geometry of the treated surface. By observing the state of the weld toe before and after the treatment, it can be seen that the shape of the toe has been deformed in correspondence to the shape of the tip of the treatment tool. The coefficient of stress concentration is the less, the larger the radius of curvature of the curved surface formed by ultrasonic impact treatment of the point of stress concentration. In the case of ultrasonic impact treatment, a magnitude of introduced compressive stress is also to be taken into consideration. Empirically, when treatment is performed with a tool having curved surface with radius of curvature (R) of about 0.5 mm~3 mm, fatigue characteristics can be improved most effectively. Therefore, a spot of stress concentration is largely treated by using a tool with this curvature.

The magnitude of introduced compressive stress can be estimated from plastic deformation of the untreated metal surface which has taken place in the direction of the depth from the surface of the metal in the treatment. Basically, it is considered that the larger the magnitude of plastic deformation in the depth direction, the larger the introduced compressive stress. However, as described above, the magnitude of plastic deformation produced by the ultrasonic impact treatment, and the effect on improvement of fatigue life, depend also on the curvature of the treatment tool. When R (radius of curvature) is small, the depth of the plastic deformation is large, and when R (radius of curvature) is large, the depth of the plastic deformation is small. Empirically, if R is about 0.5 mm~3 mm and the depth of plastic deformation is not less than 0.05 mm and not more than 1.0 mm, sufficient effect on improvement in fatigue characteristics can be obtained.

In general, the shape of the surface after treatment can be easily observed by preparing a copy of the surface using an amorphous material such as dental shaping agent. It is also possible to measure the shape directly by scanning the surface with a laser displacement meter.

When the apparatus for ultrasonic impact treatment is installed in the production line in a factory and metal products are newly produced, the inspection for crack in the pre-treatment can be replaced by visual inspection of the presence/absence of harmful defects conducted at the ordinary level of material inspection. Also, in the quality control after-treatment, as execution of ultrasonic impact treatment is evident, the post-treatment quality assurance can be replaced only by confirmation of the tool tip used in the ultrasonic impact treatment, confirmation of the output setting and visual inspection of the product for presence/absence of plastic deformation by the ultrasonic impact treatment.

In ultrasonic impact treatment that imparts compressive residual stress for improvement of fatigue life, it should be noted that the compressive residual stress introduced by the ultrasonic impact treatment in the portion of the metal subjected to ultrasonic impact treatment and the neighboring portion that may possibly affect the above-mentioned portion must not be modified in other processes such as bending, correction, heat treatment, or welding, that is necessary for producing the metal products and is accompanied by plastic deformation. Thus, it is necessary that ultrasonic impact treatment be performed after all these processes have been completed.

There are means for further enhancing the effect of treatment after predetermined performance is confirmed by the quality assurance test. Painting that is applied to the treated point may be given this function. Thus, micro-capsules that contain a paint of different color can be mixed into the painting. When the painting is stimulated externally, it becomes possible that the micro-capsules are broken and the paint of different color oozes out.

As such functional painting, a paint known as Smart Paint (e.g., U.S. Pat. No. 5,534,239), which contains micro-capsules that are broken by strain produced in the paint when a crack is generated to thereby indicate the position of a crack, may be applied to the treated spot to help visual examination and to facilitate inspection after use has started.

FIG. 1 is a flow chart showing the treatment method for improving fatigue life according to the present invention. As has been described above, the treatment method is broadly defined in the order of pre-treatment, ultrasonic impact treatment, and quality control test, so as to obtain fatigue improvement effect reliably using the characteristics of ultrasonic impact treatment.

A fatigue experiment was conducted to confirm the effect obtained by the invention. In the fatigue experiment, first a fatigue load was placed until initial fatigue is generated. Then, magnetic particle examination was performed as pre-treatment, and as, at this point, no fatigue crack was detected, removal of fatigue crack was not performed. Then ultrasonic impact treatment was performed, and thereafter, the fatigue experiment was again conducted. The fatigue crack introduced by the initial loading was rendered harmless, and fatigue life at 200 MPa was improved five times or more from 300,000 cycles to 1,500,000 cycles or more.

A feature of the present invention is that, even for fatigue cracks below detection limit, it can introduce plastic deformation and compressive stress to the tip of the crack so as to render it harmless, and unlike conventional methods, the treatment can be performed at the time of examination as a preventive measure for preventing generation of fatigue on locations where no crack can be detected. As improvement of fatigue life can be expected from this treatment, it is possible to increase the interval of regular periodical inspections regarding fatigue of the treated metal products and thereby to decrease the maintenance cost.

The maintenance cost can be also decreased by coating a functional paint that simplifies the inspection for crack after treatment.

As has been described before, metal products treated by using this invention can reliably ensure fatigue life three times or more longer than those treated by conventional methods in the ordinary used range of repeated stress.

Thus, in the treatment method for improving fatigue life according to the present invention, and metal products treated using this method, a new processing method known as ultrasonic impact treatment is combined with proper pre-treatment and quality examination method after treatment, and as a result, a remarkable effect can be obtained in that fatigue generated from metal surface can be reliably suppressed and fatigue life can be improved irrespective of whether the treatment is performed on newly produced products or on repair of products, or whether or not the product contains welded parts. Since fatigue strength can be improved even in the state where fatigue cracks of a small size and below the detection limit of conventional non-destructive tests, are left, preventive application of this treatment method for improving fatigue life to metal products before generation of detectable fatigue crack becomes possible. By applying a functional paint that helps to detect subsequent generation of cracks after treatment, maintenance cost can be decreased, especially as concerns a steel structure such as a bridge.

The invention claimed is:

1. A treatment method for improving fatigue life of a metal material characterized by comprising the steps of; for portions of the metal material for which fatigue may become a problem:
    (a) detecting a crack for the portions to be subjected to the ultrasonic impact treatment by liquid penetrant examination, magnetic particle examination or eddy current examination;
    (b) if a crack is detected, removing the crack by a grinder or by gouging;
    (c) if a removal depth is as deep as 5 mm or greater, repairing the removal portion by buildup welding;
    (d) then performing ultrasonic impact treatment; and then
    (e) confirming that a curved surface having depth of 0.05 mm or greater and a radius curvature of about 0.5 mm to 3 mm is formed at the ultrasonic impact treated surface.

2. A treatment method for improving fatigue life of a metal material according to claim 1 wherein:
    said method further comprises:
    applying a paint containing mirco-capsules to a surface of the metal material treated by said ultrasonic impact treatment;
    whereby, subsequent generation of a crack in said surface of the metal material breaks said said micro-capsules contained in the applied paint at a subsequent generated crack location, wherein a paint of different color oozes out of said broken micro-capsules, thus visually identifying said subsequent generated crack.

* * * * *